United States Patent [19]

Bruey

[11] Patent Number: 5,021,237

[45] Date of Patent: Jun. 4, 1991

[54] GEL INSECTICIDAL COMPOSITIONS

[75] Inventor: Francis J. Bruey, Bloomfield, N.J.

[73] Assignee: The Clorox Company, Oakland, Calif.

[21] Appl. No.: 441,594

[22] Filed: Nov. 27, 1989

[51] Int. Cl.$^5$ .................. A01N 25/02; A61K 31/155; A61K 37/52; A61K 9/00
[52] U.S. Cl. ........................................ 424/43; 424/45; 424/84; 514/426; 514/634
[58] Field of Search .............................. 424/43, 45, 84; 514/634, 426

[56] References Cited

U.S. PATENT DOCUMENTS

| | | | |
|---|---|---|---|
| 4,087,525 | 5/1978 | Lovell | 514/218 |
| 4,191,768 | 3/1980 | Drabb, Jr. | 514/275 |
| 4,439,342 | 3/1984 | Albanese | 424/45 |
| 4,822,613 | 4/1989 | Rodero | 424/405 |
| 4,822,614 | 4/1989 | Rodero | 424/405 |

FOREIGN PATENT DOCUMENTS

| | | | |
|---|---|---|---|
| 45-11719 | 4/1970 | Japan | 424/45 |
| 85/01876 | 5/1985 | PCT Int'l Appl. | 424/45 |
| 1159121 | 6/1981 | United Kingdom . | |

OTHER PUBLICATIONS

Chem. Ab., vol. 107, 1987, 107:231462w, Penladrenone Hydrazones As Insecticides.

*Primary Examiner*—John Doll
*Assistant Examiner*—Carmen Pili-Curtis
*Attorney, Agent, or Firm*—Harry A. Pacini; Charles J. Fickey

[57] ABSTRACT

A gel insecticide bait to be contained in a pressurized container, for dispensing a bead of gel bait in cracks, crevices and the like for destroying insects, in particular cockroaches, said composition comprising an oil-in-water emulsion of a pentadienone toxicant-fatty acid mixture in a corn syrup solution, together with a gellant.

6 Claims, No Drawings

GEL INSECTICIDAL COMPOSITIONS

The invention is an insecticidal gel composition especially useful for the control of cockroaches, a method of preparing the composition and a method of its use. More particularly, the invention relates to insecticidal gel compositions comprising a pentadienone hydrazone as a toxicant, a fatty acid, a lower alcohol, a gellant, water, a base, and a hydrocarbon propellant.

Existing insecticidal consumer pressurized sprays rely on contact mode-of-action for mortality, given only short-term efficacy against cockroaches, and may be repellant to the insect. Some of these sprays will be vaporized completely and so affect only those insects which are contacted. Others may be deposited as a liquid on surface, so that such deposits will be runny on vertical or overhead surfaces, and on non-absorbent surfaces. Such liquid deposits will also be absorbed into absorbent surfaces such as wood or wallpaper. Thus these sprays will have little if any residual activity. The present invention exploits the insects feeding behavior to administer the pesticide to the insect, and provides a residue of long-lasting effectiveness. The present invention provides a stable formulation for aerosol packaging.

A novel insecticidal gel compositions of the invention are suitable for application within and around cockroach habitats. This type of application requires compositions which possess physical properties which make them suitable for application as a bead of material in corners and hard to reach places within structures which are inhabited by cockroaches.

Pressurized spray gel bait allows delivery of non-repellent, longlasting insecticidal bait into structural cracks and voids that harbor cockroaches.

This requires that the composition be sufficiently fluent to be dispensed from a pressurized package, and be deposited in a form which will retain sufficient bulk to be ingested by cockroaches over a long period.

In copending, commonly assigned application Ser. No. 442,024, filed Nov. 27, 1989, was disclosed an aerosol foam composition. It has been found that although such foams are effective, they collapse to a thin film and this is not an ideal form for the cockroach to pick up with its mouth parts. The gel bait of the present invention retains its bulk for a longer time, thus making it easy for the roach to ingest. On the other hand, the gel is not dispensable as an aerosol since the mixing of the propellant gas with the composition would tend to create a foam upon dispensing. In the present application, the gel composition is dispersed from a sepro dispenser (well known in the art) can, which has an internal bladder filled with the gel. The bladder is surrounded by an inert gas under pressure, e.g. carbon dioxide or nitrogen. Gas compresses the bladder to expel product when the container valve is opened.

The invention can be applied to residential as well as industrial cockroach infestations for long-term control. The invention provides a means of delivering a poison cockroach bait in viscid form in situations where solid or liquid forms are not suitable. Many species of pest insect are susceptible to control by the invention. It is particularly useful against cockroaches.

This invention has the following advantages over aerosol contact and residual sprays and current bait tray technology.

The preparation is non-repellant. There is a higher frequency of bait placement yielding more complete treatment and control. The bait material can be placed in closer proximity to harborages than standard bait trays permitting tailoring of the bait application of structural idiosyncracies, enhancing the frequency that foraging insects will encounter the bait. The bait material is delivered in such a form and remains in such a form as to be readily available for ingestion by insects. Long term efficacy can be achieved.

The present gel bait composition comprises an oil-in-water emulsion of a toxicant—fatty acid mixture in a corn syrup solution. The ingredients and their amounts are set forth in Table I as follows:

The gel bait ingredients and their amounts are set forth in Table I below.

TABLE I

| GEL BAIT FORMULATION | | | |
|---|---|---|---|
| INGREDIENT | FUNCTION | PREFERRED AMOUNT | RANGE |
| Sugar Syrup @ 70-80% Solids (Preferably Isomerose Corn Syrup) | Food Substance | 30% | 20-40% |
| Pentadienone (Compound CL 217,300) | Toxicant (Non-Repellant) | 0.60% | 0.25-1.00% |
| Stearic Acid | Toxicant Solubilizer Gellant | 2.40% | 2.3-4.0% |
| Alcohol (Ethanol, Isopraponal) | Toxicant Solubilizer | 6.0% | 5-7% |
| Antimicrobial Agents | | | |
| Preferably (Methylparaben) | | 0.20% | 0.15-0.25% |
| (Propylparaben) | | 0.15% | 0.10-0.20% |
| Surfactant | | | |
| (Preferably Ethoxylated Cetyl/Stearyl Alcohol Blend) | Dispersant | 3.0% | 2.0-4.0% |
| Water | Solvent | 56.33% | 50-65% |
| Base | | | |
| (Preferably Potassium Hydroxide, 45% Solution) | Adjustment | 0.22% | 0.20-0.30% |
| Polydimethyl Siloxane Antifoam Emulsion* | Processing Aid | 0.10% | 0.00-0.20% |
| Glycerin | Optional Humectant | 1.00% | 0-5% |
| Hydrocarbon | | | |
| Preferably Isobutane/Propane Blend, 46 PSIG Vapor Pressure @ 70° F. 41.53 | Propellant | 5% | 3-7% |

*The polydimethyl siloxane is added during processing only to prevent excess foaming and is not a functional ingredient of the product.

The pentadienone poison is an insecticide which is active as a stomach poison.

Pentadiene-3-one substituted amidinohydrazones are described by Tomcufcuk, U.S. Pat. No. 3,878,201, as antimalarial and anti-tubercular agents. Lovell, U.S. Pat. Nos. 4,087,525 and 4,163,102—the disclosures of which are incorporated hereby reference thereto, describes the use of these compounds of the Lovell patents are generally represented by the formula:

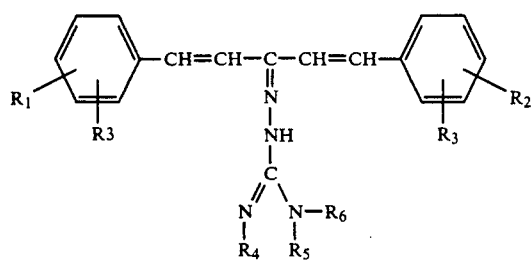

wherein $R_1$ and $R_2$ each represent hydrogen, halogen, the group $-CF_3'C_1-C_4$ alkyl, $C_1-C_4$ alkoxy, or $C_1-C_4$ alkylthio; $R_3$ is hydrogen or methyl, provided that when $R_3$ is methyl both $R_1$ and $R_2$ are also methyl; $R_4$ and $R_5$ represent hydrogen, $C_1-C_4$ alkyl or when taken together, an alkylene group of 2 to 6 carbon atoms, methyl or phenyl alkylene group of 2 to 6 carbon atoms or 1, 2-cyclohexylene; $R_6$ is hydrogen or $C_1-C_4$ alkyl; and salts thereof.

Particularly useful compounds are those represented by the formula:

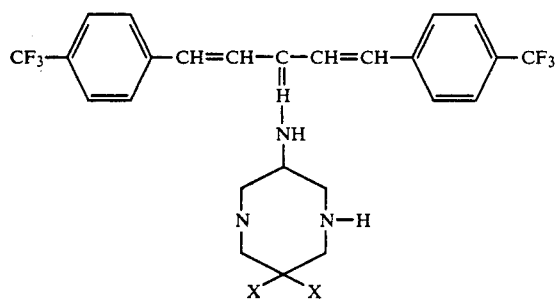

compound represented by Formulas (I) an (II) against a variety of Lepidopterous, Orthopterous, Dipterous and Hymenopterous insects is also described by Lovell.

However, the form and method of use described in these patents is generally related to agricultural applications where particulate baits are used and distributed over wide, open areas, and the types of bait system suggested therein are clearly not suitable for general household consumer use.

A gel formulation was prepared and evaluated as shown in the following Examples.

EXAMPLE I

A gel bait composition was prepared having the following composition for use in a:

|  | % |
| --- | --- |
| Corn Syrup | 30.00 |
| Pentadienone (CL 217,300) | 0.60 |
| Stearic Acid | 2.40 |
| Propanol | 6.00 |
| Propyl Paraben | 0.15 |
| Methyl Paraben | 0.20 |
| Ethoxylated Cetyl/Stearyl Alcohol | 3.00 |
| Potassium Hydroxide (45% solution) | 0.22 |
| Water | q.s. |
|  | 100.00 |

EXAMPLE II

The aerosol gel bait of Example I was tested in the laboratory against German roaches and compared with a foam bait disclosed in commonly assigned copending application Ser. No. 442,024 filed Nov. 27, 1989, and against a solid bait in a feed station disclosed in U.S. Pat. No. 4,563,836, issued Jan. 14, 1986.

LABORATORY EVALUATION OF EFFICACY COMPARISON ROACH CONTROL FOAM BAIT (MFB/CPRD 13567) ROACH CONTROL GEL BAIT (MFB/CPRD 13581)

Summary

Gel bait was shown to be efficacious when tested in laboratory model infestations of German cockroaches. The product yields high levels of cockroach population reduction, comparable to the reductions provided by COMBAT Roach Control Bait Trays and foam bait under a variety of circumstances.

Materials and Methods

Products are tested against laboratory model infestations comprising populations of German cockroaches confined in test arenas and provided with harborage, water, and an abundant supply of alternate food. Test arenas consist of 18" square areas bounded by glass walls 6" high greased with a mixture of petrolatum and mineral oil to prevent cockroach escape Each arena contains a cardboard box ($2\frac{3}{4}"\times 5\frac{1}{4}"\times 7\frac{3}{4}"$) harborage provided with an entrance slit and a liner of pleated corrugated cardboard strip ($1\frac{1}{2}"\times 18"$) and a 2 oz. water bottle with paper towel wick. Harborage and water bottle are disposed against one wall of the arena. An alternate food supply of approximately 20 nuggets of PURINA ® Cat Chow is distributed around the harborage entrance. Populations of approximately 25 German cockroaches of mixed ages and both sexes are installed in each arena by random allocation of a representative sample drawn from a rearing facility. Cockroach populations are installed approximately four days prior to the introduction of bait treatments into the arenas. Arenas are maintained at room temperature (70°-80° F.) throughout the test period.

Bait treatments are applied to model baseboards consisting of 2–3"×6" pieces of unfinished $\frac{1}{4}"$ plywood glued along a long edge to form an L-shaped profile or to glass plates 6" square. Baits are applied at the rate of approximately 5 grams of product per arena. Bait treatments are assigned to arenas in a completely randomized manner.

Mortality in each arena is assessed seven days after the introduction of bait treatments. Cockroaches not responding with greater than one body-length of escape motion upon prodding of cerci by forceps are classified as dead.

Results

1. Tests of fresh deposits on wood of fresh preparations of Foam Bait (CPRD 13567) and (Gel Bait CPRD 13581) in comparison with single bait tray treatment with COMBAT Roach Control Bait Tray (Test 1987-147).

| Product | % Mortality |
| --- | --- |
| Foam | 75% |

| Product | % Mortality |
| --- | --- |
| Gel | 88% |
| Bait Tray | 68% |

2. Test of fresh deposits on wood from packages of product aged for one-month at stated temperature, in comparison with single bait tray treatment (TEST 1987-137).

| Product | % Mortality |
| --- | --- |
| Foam-Room Temperature | 68% |
| Foam-45° | 68% |
| Gel-Room Temperature | 73% |
| Gel-45° C. | 93% |
| Bait Tray | 93% |

3. Test of fresh deposits on wood from packages of product aged for two months at stated temperature, in comparison with single bait tray treatment (Test 1987-151).

| Product | % Mortality |
| --- | --- |
| Foam-Room Temperature | 72% |
| Foam-45° C. | 77% |
| Gel-Room Temperature | 83% |
| Bait Tray | 75% |

4. Test of deposits of bait aged for one month at room temperature on stated surface (Test 1987-154).

| Product | Surface | % Mortality |
| --- | --- | --- |
| Foam | Glass | 65% |
| Foam | Wood | 88% |
| Gel | Glass | 64% |
| Gel | Wood | 88% |

*Deposits on wood significantly more efficacious in this test, probably due to deposit orientation in arena. Products yield equivalent efficacy.

5. Test of deposits of bait aged for three months at room temperature on stated surface (Test 1987-179).

| Product | Surface | % Mortality |
| --- | --- | --- |
| Foam | Glass | 79% |
| Foam | Wood | 63% |
| Gel | Glass | 96% |
| Gel | Wood | 96% |

*Gel yields significantly superior efficacy in this test. Surface has no effect in this test.

Conclusion

Efficacy provided by the gel bait in laboratory tests is generally equal to or superior to the foam bait of copending application Ser. No. 442,024, to and COMBAT Roach Control Bait Trays.

EXAMPLE III

LABORATORY EVALUATION OF EFFICACY OF GEL AND ROACH CONTROL FOAM, BAITS, AGAINST AMERICAN COCKROACHES

Summary

The foam and gel baits of Example II were tested in laboratory model infestations of American cockroaches.

Material and Methods

Products are tested against laboratory model infestations comprising populations of American cockroaches confined to test arenas and provided with harborage, water, and an abundant supply of alternate food. Test arenas consist of 18" square areas bounded by glass walls 6" high greased with a mixture of petrolatum and mineral oil to prevent cockroach escape. Each arena contains harborage in the form of 2 square feet of shredded corrugated cardboard massed in the center of the arena, a 2 oz. water bottle with paper towel wick and alternate food in the form of 8 level teaspoons of a 50/50 blend of ground PURINA cat chow and granulated sugar sprinkled over the shredded cardboard. Populations of approximately ten cockroaches of mixed age/sex are installed in the arenas in the test in a randomized manner several days before treatments are introduced.

Bait treatments are applied to unfinished plywood boards $\frac{1}{4}"\times 3"\times 6"$ at a rate of 10 grams of product per arena. Mortality is assessed fourteen days after bait application.

Results (Test 1987-184)
| Product | % Mortality, 14 Days |
| --- | --- |
| Foam | 70% |
| Gel | 58% |
| No Treatment | 0% |

EXAMPLE IV

Roach Control Foam Bait, MFB/CPRD 13567

Roach Control Gel Bait, MFB/CPRD 13581

Field Efficacy Trials Report

Field trails at Texas A&M University, College Station, Tex.

Summary

Field trials of Roach Foam Bait and Gel Baits of Example II were conducted in student housing on the campus of Texas A&M University, College Station, Tex., to demonstrate product efficacy in the reduction of household infestations of German cockroaches. Reductions in sticky-tray counts of cockroaches averaging 91% for Foam Bait and 88% for Gel Bait were achieved. Large reductions in counts were achieved within two weeks of product application and were sustained for the entire three-month post-application test period.

Materials and Methods

Sixty apartments comprising married student housing on the campus of Texas A&M University were identified by the Dept. of Entomology, Tex. A&M University, as having German cockroach infestations suitable for test purposes. Pretest counts, obtained by summing over the three RAID ® Roach traps in place in each apartment kitchen for a period of 18 to 24 hours, averaged 25 per apartment, ranging from 1 to 194. The set of apartments was ranked from high to low precounts and divided into 10 blocks of six apartments of comparable infestation level, to which the six treatments under study were assigned in a random manner. The apartments were structurally sound and representative of a normal range of sanitation and clutter.

The six treatments under study included Foam Bait and Gel Bait, COMBAT Roach Control Bait trays as a control, RAID Ant and Roach Killer as a control, an experimental formulation and a placebo treatment consisting of COMBAT Roach Control Bait Trays without bait. Product applications were confined to kitchen areas, based on cooperator assurances that infestation levels at other locations in the apartments were negligible. Approximately 11 wt. oz. per apartment of Foam Bait and Gel Bait were applied to inaccessible places, with much of the placement concentrated as large deposits in cabinetry framework behind drawers and beneath the sink, behind the stove, and behind and beneath the refrigerator. Applications of small amounts of bait were made to deep corners in cabinets and to hinges of cabinet doors. Structural cracks an crevices, when present, were fully exploited for bait placement. Such placement was appreciable in about one-third of the apartments. Baseboard application was avoided. Approximately 5 to 6 wt. oz. of RAID Ant and Roach Killer was applied per apartment, representing the maximum feasible product usage in the kitchen. Drawers were removed from cabinetry and their outer surfaces sprayed. Applications to cupboards were restricted to brief spray bursts delivered to the hinges and edges of doors. Thorough coverage under the sink, behind the refrigerator and along baseboards was provided. Applications of all spray products were adjusted from apartment to apartment to accommodate the different patterns of kitchen storage space utilization, but an overall consistency of application technique was maintained. COMBAT Roach Control bait trays were applied as directed, with one each behind the stove and refrigerator, two under the sink, and the remainder in the cabinets and cupboards.

At the time points 2 weeks, 4 weeks, 8 weeks and 12 weeks after product application, counts of cockroaches were obtained using RAID Roach Traps in the same locations used for precounts, again in place for 18 to 24 hours. At the 4 week time point, occupants of apartments treated with RAID Ant and Roach were given fresh RAID cans (one per apartment) and instructions to "spray as necessary."

Results

All COMBAT products tested provided large reductions in trap counts. Foam Bait and Gel Bait provided percent reductions unsurpassed by any product in the test, comparable to the reductions provided by the COMBAT Roach Control Bait Trays and significantly superior to reductions provided by RAID Ant and Roach Killer and to reductions observed in apartments receiving no pesticidal treatment (placebo product). Large reductions were noted as early as two weeks after product application, with minimum reductions observed at the one-month monitoring point. These reductions were subsequently maintained throughout the three month test period. Estimates of the test-wide average percent reduction in counts for each product are given in Table II. Estimates of the average percent reduction in counts at each postcount time point are given in Table III.

Reductions were noted as early as two weeks after product application, with minimum reductions observed at the one-month monitoring point. These reductions were subsequently maintained throughout the three month test period. Estimates of the test-wide average percent reduction in counts for each product are given in Table II. Estimates of the average percent reduction in counts at each postcount time point are given in Table III.

TABLE II

| Test-Wide Average Percent Reductions in Counts | |
|---|---|
| Foam Bait | 91% |
| Gel Bait | 88% |
| COMBAT Trays | 72% |
| RAID Ant and Roach Killer | 42% |
| Placebo Treatment | 42% |

TABLE III

| | Average Percent Reduction in Counts | | | |
|---|---|---|---|---|
| | 2 Weeks | 4 Weeks | 8 Weeks | 12 Weeks |
| Foam Bait | 89% | 93% | 89% | 91% |
| Gel Bait | 92% | 91% | 85% | 80% |
| COMBAT Trays | 62% | 81% | 61% | 79% |
| RAID A&R Killer | 26% | 63% | 27% | 43% |
| Placebo | 41% | 35% | 44% | 46% |

Example II, III and IV illustrate the increase efficaciousness of the pressurized gel method of bait placement, as compared to aerosol direct insecticide spraying aerosol foam and spot placement of ingestible bait containing a pesticide.

We claim:

1. An insecticidal gel composition for aerosol application for destroying cockroaches which comprises, by weight, 20 to 40% of a sugar, 0.25 to 1% of a pentadienone insecticide, 2.3–4% stearic acid, 5 to 7% of ethanol or propanol, 0.15 to 0.2% of an antimicrobial agent, about 3.0% cetyl/stearyl alcohol, 50% to 65% water, 0.2 to 0.36% of a base, 0.05 to 0.20% polydimethyl siloxane, 0 to 5% glycerin, and 3 to 7% propane.

2. The composition of claim 1 comprising in addition an antimicrobial agent and a humectant.

3. The composition of claim 1 wherein said pentadienone is a compound of the formula:

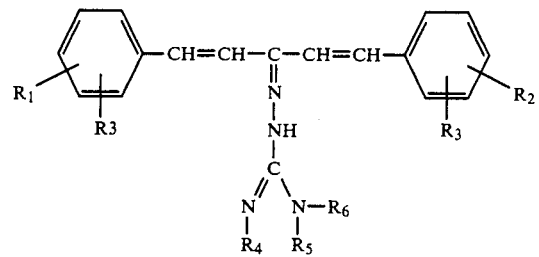

wherein $R_1$ and $R_2$ each represent hydrogen, halogen, the group $-CF_3$, $C_1-C_4$ alkyl, $C_1-C_4$ alkyoxy, or $C_1-C_4$ alkylthio; $R_3$ is hydrogen or methyl, provided that when $R_3$ is methyl both $R_1$ and $R_2$ are also methyl; $R_4$ and $R_5$ represent hydrogen, $C_1-C_4$ alkyl or, when taken together, an alkylene group of 2 to 6 carbon atoms, methyl or phenyl alkylene group of 2 to 4 carbon atoms or 1,2-cyclohexylene; $R_6$ is hydrogen or $C_1-C_4$ alkyl; and salts thereof.

4. The composition of claim 3 wherein said base is potassium hydroxide.

5. A method for destroying cockroaches which comprises dispensing the composition of claim 1 from a pressurized container and depositing said composition as a solid bead of material along cracks and crevices of cockroach harborages.

6. The method for destroying cockroaches which comprises dispensing the composition of claim 1 from a pressurized container and depositing said composition as a solid bead of material along cracks and crevices of cockroach harborages.

* * * * *